United States Patent

Kanda et al.

Patent Number: 4,730,057
Date of Patent: Mar. 8, 1988

[54] PHTHALIDE DERIVATIVES USEFUL AS COLORLESS CHROMOGENIC MATERIAL

[75] Inventors: Nobuo Kanda, Osaka; Naoki Yonese; Mitsuru Kondo, both of Hyogo, all of Japan

[73] Assignee: Kanzaki Paper Manufacturing Co., Ltd., Tokyo, Japan

[21] Appl. No.: 817,564

[22] Filed: Jan. 10, 1986

[30] Foreign Application Priority Data

Jan. 17, 1985 [JP] Japan .................................. 60-7074
Jan. 17, 1985 [JP] Japan .................................. 60-7075

[51] Int. Cl.⁴ .............................................. C07D 295/06
[52] U.S. Cl. .................................... 548/524; 548/523; 546/166; 546/94; 427/150
[58] Field of Search .............................. 548/523, 524

[56] References Cited

U.S. PATENT DOCUMENTS 4,107,428 8/1978 Farber .................................. 542/437

FOREIGN PATENT DOCUMENTS 62544 4/1982 European Pat. Off. ............ 542/437

Primary Examiner—Alan L. Rotman
Assistant Examiner—J. Richter
Attorney, Agent, or Firm—Fisher, Christen & Sabol

[57] ABSTRACT

A new phthalide derivative useful as a colorless chromogenic material has the following formula:

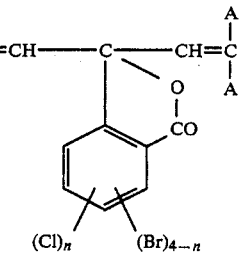

wherein A and n have the same meaning as defined hereinbefore.

1 Claim, No Drawings

PHTHALIDE DERIVATIVES USEFUL AS COLORLESS CHROMOGENIC MATERIAL

BACKGROUND OF THE INVENTION

This invention relates to phthalide derivatives as new compounds useful as colorless chromogenic materials, a new process for preparing the same, and a new recording system utilizing the same.

There are known various kinds of recording systems utilizing the colorforming reaction between a colorless chromogenic material and an electron accepting acidic reactant material by the medium of mechanical, heat, electric or light energy. Among them there are included a pressure sensitive record sheet, a heat sensitive record sheet, an electrothermal record sheet, an ultrasonic record sheet, an electron beam record sheet, an electrostatic record sheet and a photosensitive record sheet. The colorless chromogenic materials of these kinds also find their usefulness in typewriter ribbons, ball-point pen ink, crayon and stamp ink.

One of the most typical colorless chromogenic materials is crystal violet lactone. This dye material reacts with an electron accepting acidic reactant material upon contact to develop a clear color of bluish violet but the developed color has a poor light resistance so that the recorded images (color images) soon disappear in a short time when subjected to radiation of ultraviolet rays of day light. Another disadvantage of this type of dye is in the fact that the recorded images obtained with this material show no absorption for the infrared range of 700-900 nm and accordingly this type of dye material cannot be used for a reading machine utilizing an optical reading system responsive to infrared absorption.

Recently, we have proposed certain kinds of phthalide derivatives having two vinyl linkages as substantially colorless chromogenic material which are adapted for optical reading with near infrared rays in EP Application No. 82301885.8 (EP Publication No. 62544).

However, the record materials such as heat-sensitive record materials in which any of those phthalide derivatives is used are easily affected by temperature and humidity so that fogging occures and the produced color image is discolored. Resultantly, the difference between the light absorptions of the produced color image and the background at near infrared wavelength become too small to adapt them for optical reading. Further, if the produced color images exposes to light, the light absorbability of near infrared wavelength is liable to disappear so that it become difficult to adapt them for optical reading as described above. In addition, color developing on the background and discoloration of the produced color images easily occur by finger-print.

The primary object of the invention is to provide novel phthalide derivatives superior in both of heat resistance and moisture resistance and useful as colorless chromogenic materials for use in various recording systems.

Another object of the invention is to provide novel colorless chromogenic material for use in recording systems in which the color images when developed therefrom have a good light resistance, especially, a good ultraviolet ray resistance.

A further object of the invention is to provide novel colorless chromogenic materials for use in recording systems in which the color images when developed therefrom show a good absorption for infrared rays.

A still further object of the invention is to provide a novel process for preparing phthalide derivatives of the kind described above.

It is also included among the objects of the invention to provide an improved recording system in which a phthalide derivative as a new compound is used as a colorless chromogenic material and the color images when developed therefrom have a good light resistance and show a good absorption for infrared rays.

Other objects and advantages of the invention will become apparent from the following description.

SUMMARY OF THE INVENTION

The novel phthalide derivatives according to the invention has the following formula:

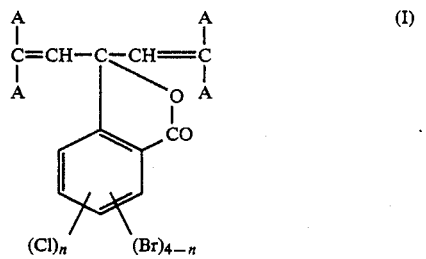

wherein A is

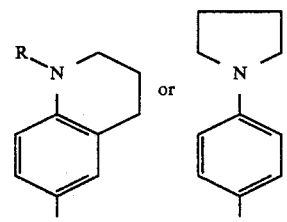

R is an alkyl group having 1 to 4 carbon atoms or a propylene group which may form julolidine ring together with the adjacent benzene ring, and n is 0 or an integer of 1 to 4 when A is

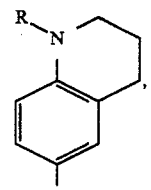

but n is an integer of 1 to 3 when A is

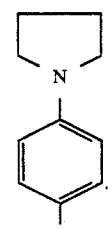

The phthalide derivative having the above general formula can be used as colorless chromogenic materials for use in various recording systems including a pressure sensitive recording system and a heat sensitive recording system. The compounds according to the invention can produce a clear and deep greenish color upon contact with an electron accepting acidic reactant material. The record materials comprising the phthalide derivatives according to the invention as chromogenic materials are stable under the circumstances of high humidity and high temperature. The produced color images have a good light resistance and can maintain the clear color tone initially produced for a long time. The color images also show a good absorption for infrared rays with the range of 700–900 nm so that they can be detected for reading in an infrared ray responsive optical reading machine.

DETAILED DESCRIPTION OF THE INVENTION

In one aspect of the invention the novel phthalide derivatives are represented by the following formula:

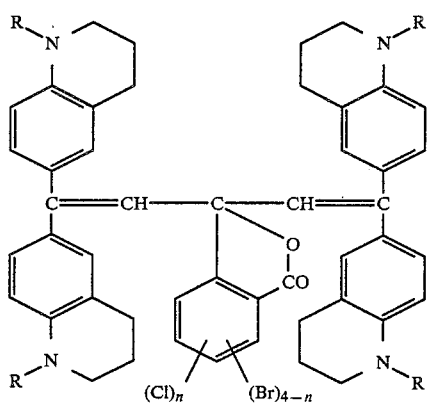

(IV)

wherein n is 0 or an integer of 1 to 4.

In another aspect of the invention the novel phthalide derivatives are represented by the following formula:

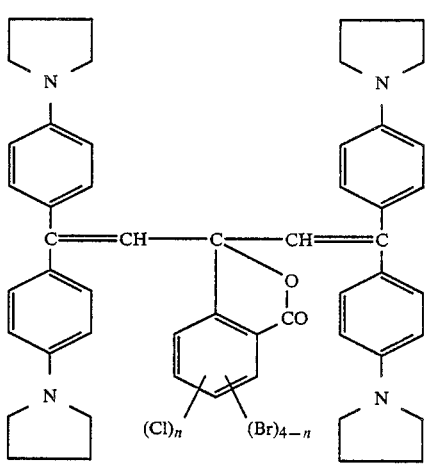

(V)

wherein n is an integer of 1 to 3.

The compounds represented by the formula (I) may preferably be prepared by making phthalic acid anhydrides represented by the formula (II) react with ethylene derivatives represented by the formula (III) with use of dehydration condensation agents at a temperature within the range of 50° C. to 200° C. and for scores of minutes to several hours:

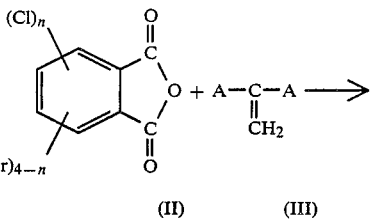

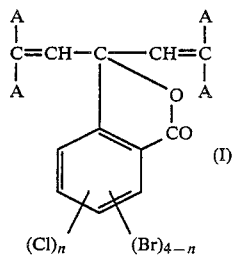

(I)

wherein A is

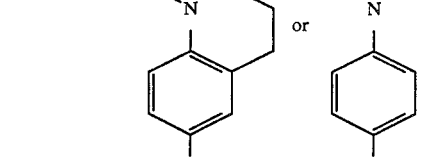

R is an alkyl group having 1 to 4 carbon atoms or a propylene group which may form together the adjacent benzene ring julolidine ring, and n is 0 or an integer of 1 to 4 when A is

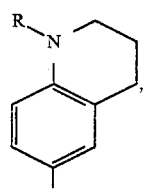

but n is an integer of 1 to 3 when A is

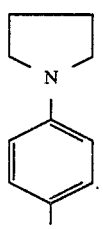

As the dehydration condensation agents for carrying out the reaction between phthalic anhydride derivatives and ethylene derivatives, there are preferably used those having a function as a solvent, such as lower fatty acid anhydride, e.g., acetic anhydride and propionic anhydride, and inorganic acid, e.g., phosphorus oxychloride, phosphorus trichloride, sulfuric acid and polyphosphoric acid. Various Friedel-Crafts Type Catalysts may also be used as dehydration condensation agents. These dehydration condensation agents may be used either solely or in combination.

The phthalide derivatives thus obtained according to the invention are substantially colorless chromogenic compounds having very superior properties. For example, the heat-sensitive record materials using the phthalide derivatives are superior in heat resistance and moisture resistance to those using the other phthalide derivatives. Accordinly, they do not have a tendency of fogging on the background and discoloration of the produced color images and further the produced color images have a good light resistance. Especially, the phthalide derivatives having both of Cl and Br in the molecule is preferred, because of producing the record materials improved in fogging properties, color-developability, heat resistance, moisture resistance, light resistance and the like with a good balance. 3,3-bis[1,1-bis(4-pyrrolidinophenyl)ethylene-2-yl]-phthalide derivatives having both of Cl and Br in the molecule are the most preferable. The compounds are very superior in heat resistance and moisture resistance and stable for a long time. With use of the compounds, heat-sensitive record materials can be produced without being affected by fingerprint.

Further, the pressure-sensitive record materials obtained by using the phthalide derivatives according to the invention produce color images superior in light resistance. Especially, 3,3-bis[1,1-bis(4-pyrrolidinophenyl)ethylene-2-yl]-phthalide derivatives having both of Cl and Br in the molecule are the most preferable, because of having a good solubility to the solvent used for producing pressure-sensitive record mateirals.

As described above, the phthalide derivatives according to the invention are useful as chromogenic materials for producing record materials utilizing the colorforming reaction between a colorless chromogenic material and an electron accepting materials (hereinafter referred to as "acceptors").

The above mentioned phthalide derivatives may be used either solely or in combination or, when desired, together with any of the following basic dye compounds: triarylmethanelactone compounds such as 3,3-bis(p-dimethylaminophenyl)-6-dimethylaminophthalide, 3-(p-dibenzylaminophenyl)-3-(1,2-dimethylindole-3-yl)-7-azaphthalide, 3-(4-diethylamino-2-ethoxyphenyl)-3-(1-ethyl-2-methylindole-3-yl)-7-azaphthalide and 3,3-bis(1-ethyl-2-methylindole-3-yl)-phthalide; fluoran compounds such as 3-diethylamino-6-methylfluoran, 3-diethylamino-6-methyl-7-chlorofluoran, 3-(N-ethyl-N-p-tolylamino)-7-methylfluoran, 3-diethylamino-6-methyl-7-anilinofluoran, 3-(N-ethyl-N-i-pentylamino)-6-methyl-7-anilinofluoran, 3-(N-ethyl-N-tetrahydrofurfurylamino)-6-methyl-7-anilinofluoran, 3-(N-cyclohexyl-N-methylamino)-6-methyl-7-anilinofluoran, 3-(N-ethyl-N-p-tolylamino)-6-methyl-7-anilinofluoran, 3-diethylamino-6-chloro-7-anilinofluoran, 3-dibutylamino-7-o-chloroanilinofluoran and 3-dibutylamino-7-o-fluoroanilinofluoran; spiropyran compounds such as di-β-naphthospiropyran and 3-methyl-di-β-naphthospiropyran; diphenylmethane compounds such as 4,4'-bis-dimethylaminobenzhydrylbenzyl ether and 4,4'-bis-dimethylaminobenzhydryl-p-toluenesulfinic acid ester; azine compounds such as 3,7-bis(dimethylamino)-10-benzoylphenothiazine and 3,7-bis-(diethylamino)-10-benzoylphenoxazine; and triarylmethane compounds such as N-butyl-3[bis{4-(N-methylanilino)-phenyl}methyl]-carbazole.

The acceptors used are selected according to the kinds of record materials. The materials which are preferably used as acceptors for pressure sensitive record materials, heat sensitive record materials, electrothermal record materials, ultrasonic record materials, electrostatic record materials, typewriter's ribbons, ballpoint pen ink and crayon are those which function as Brønsted or Lewis acid. Among them there are included: inorganic acceptors such as acid clay, activated clay, attapulgite, bentonite, colloidal silica, aluminum silicate, magnesium silicate, zinc silicate, tin silicate, calcined kaolin and talc; organic acceptors such as aliphatic carboxylic acids, e.g., oxalic acid, maleic acid, tartaric acid, citric acid, succinic acid and stearic acid, aromatic carboxylic acids, e.g., benzoic acid, p-tert-butylbenzoic acid, phthalic acid, gallic acid, salicylic acid, 3-isopropylsalicylic acid, 3-phenylsalicylic acid, 3-cyclohexylsalicylic acid, 3,5-di-tert-butylsalicylic acid, 3-methyl-5-benzylsalicylic acid, 3-phenyl-5-($\alpha,\alpha$-dimethylbenzyl)salicylic acid, 3,5-di($\alpha$-methylbenzyl)-salicylic acid and 2-hydroxy-1-benzyl-3-naphthoic acid, phenolic compounds, e.g., 4,4'-isopropylidenediphenol, 4,4'-isopropylidenebis(2-chlorophenol), 4,4'-isopropylidenebis(2,6-dibromophenol), 4,4'-isopropylidenebis(2,6-dichlorophenol), 4,4'-isopropylidenebis(2-methylphenol), 4,4'-isopropylidenebis(2,6-dimethylphenol), 4,4'-isopropylidenebis(2-tert-butylphenol), 4,4'-sec-butylidenebisphenol, 4,4'-cyclohexylidenebisphenol, 4,4'-cyclohexylidenebis(2-methylphenol), 4-tert-butylphenol, 4-phenylphenol, 4-hydroxydiphenoxide, α-naphthol, β-naphthol, methyl 4-hydroxybenzoate, benzyl 4-hydroxybenzoate, 2,2'-thiobis(4,6-dichlorophenol), 4-tert-octylcatechol, 2,2'-methylenebis(4-chlorophenol), 2,2'-methylenebis(4-methyl-6-tert-butylphenol), 2,2'-dihydroxydiphenyl, 4-hydroxydiphenyl sulfone and 4-hydroxy-4'-methyldiphenyl sulfone, phenol resins, e.g., p-phenylphenol-formaldehyde resin and p-butylphenol-acetylene resin; salts of the above organic acceotors with polyvalent metals such as zinc, magnesium, aluminium, calcium, titanium, manganese, tin and nickel; and inorganic acid such as hydrogen halide, e.g., hydrogen chloride, hydrogen bromide and hydrogen iodide, boric acid, silicic acid, phosphoric acid, sulfuric acid, nitric acid, perchloric acid and halides of aluminium, zinc, nickel, tin, titanium, boron and the like.

In the case of electron beam record materials or photosensitive record materials, compounds which can produce by electron beam or light radiation hydrogen halogenides, such as hydrogen chloride, hydrogen bromide and hydrogen iodide, carboxylic acids, sulfonic acids or phenols are preferably used as acceptor materials. Among those compounds, there are included organic halogen compounds, such as carbon tetrabromide, $\alpha,\alpha,\alpha$-tribromoacetophenone, hexachloroethane, iodoform, 2-tribromomethylpyridine, trichloromethyl sulfonylbenzene, o-quinonediazido compounds, phenol esters of carboxylic acid or sulfonic acid which can cause Fries rearrangement.

Some embodiments of the utilization of the phthalide derivatives according to the invention for various kinds of record materials are described hereinbelow:

The phthalide derivatives can be utilized for various kinds of pressure sensitive record materials, e.g., those disclosed in U.S. Pat. Nos. 2,505,470, 2,505,471, 2,505,489, 2,548,366, 2,712,507, 2,730,456, 2,730,457, 3,418,250, 3,924,027 and 4,010,038.

A typical method for the production of a pressure sensitive record material utilizing the phthalide derivatives according to the invention is as follows:

At least of the phthalide derivatives according to the invention is dissolved in a solvent to form a solution which may include synthetic oil such as alkylated naphthalene, alkylated diphenyl, alkylated diphenylmethane and alkylated terphenyl, vegetable oil such as cotton seed oil and castor oil, animal oil and mineral oil or mixtures of the foregoing. The solution may additionally include basic colorless chromogenic material such as triarylmethane lactones, spiropyrans, fluorans, diphenylmethanes and azines. The solution of the phthalide derivative may be dispersed in a binder to form a coating composition. The solution may be enclosed in microcapsules through the utilization of the coacervation technique, the interfacial polymerization technique, the in-situ polymerization technique or any other method for making oil droplet-containing microcapsules and the microcapsules thus prepared are dispersed in a binder to form a coating composition. Any one of the coating compositions thus prepared is applied to a base sheet such as a paper sheet, plastic sheet, resin coated paper sheet, etc. to obtain a pressure sensitive record material. In case where the pressure sensitive copying system consisits of a top sheet, a bottom sheet and, if necessary, at least one middle sheet, the pressure sensitive record material according to the invention is used as the top sheet and the middle sheet. The pressure sensitivie record material according to the invention also be utilized in the "self contained" system in which both the colorless chromogenic material and the acceptor are dispersed on one surface of the same sheet. The pressure sensitive record material utilizing the phthalide derivative according to the invention can produce clear color images having a good light resistance and showing a good absorption for infrared rays which enables a certain reading by an optical reading machine.

The phthalide derivatives according to the invention are also useful for production of various kinds of heat sensitive record materials, e.g., as disclosed in Japanese Patent Pablications Nos. 3,680 of 1969, 27,880 of 1969, 14,039 of 1970, 43,830 of 1973, 69 of 1974, 70 of 1974 and 20,142 of 1977.

Most typically, heat sensitive record materials may be produced by coating a coating composition including fine particles of basic chromogenic material comprising the phthalide derivative according to the invention, an acceptor and a binder on a base sheet such as paper sheet, plastic film, synthetic paper sheet, woven fabric sheet or mold. The amount of the acceptor in the recording layer may be within the range of 1 to 50 parts by weight, preferably within the range of 2 to 10 parts by weight, per one part by weight of the basic chromogenic material used.

The coating composition may include inorganic metal compounds such as oxides, hydroxides and carbonates of polyvalent metals and/or inorganic pigments in an amount of 0.1 to 5 parts by weight, preferably, 0.2 to 2 parts by weight, per one part by weight of the amount of the acceptor. Further, the recording layer may also include dispersing agents, ultraviolet ray absorbing agents, heat fusible materials, antifoaming agent, fluorescent dye, coloring dyes and other adding materials. The phthalide derivative and the acceptor may be applied to a base sheet either in the form of a single coating composition or in the form of two separate coating compositions which may be applied one by one. Application of the phthalide derivative and acceptor to a base sheet may also be carried out by impregnation or by sizing. The amount of the coating composition including the phthalide derivative and the acceptor may preferably be within the range of 2 to 12 g/cm$^2$. Among the useful binder materials there may be included starches, celluloses, proteins, gum arabic, polyvinyl alcohol, salts of styrene-maleic anhydride copolymer, styrene-butadiene copolymer emulsions, salts of vinyl acetate-maleic anhydride copolymer and salts of polyacrylic acid.

The electrothermal record materials may be produced according to any known methods such as those disclosed in Japanese Laid-Open Patent Publications Nos. 11,344 of 1974 and 48,930 of 1975. Usually, the record material of this type may be produced, either by coating on a base sheet such as a paper sheet a coating composition essentially consisting of a dispersion of an electroconductive material, a basic chromogenic material comprising the phthalide derivative according to the invention, an acceptor and a binder, or by coating an electroconductive material on a base sheet to form an electroconductive layer thereon and further coating on the electroconductive layer another coating composition essentially consisting of a dispersion of the phthalide derivative according to the invention, an acceptor and a binder. In case where each of the phthalide derivative and the acceptor used is not fusible within the temperature range of 70° to 120° C., an appropriate heat fusible material may be added for controlling the heat sensitivity.

The photosensitive record materials in which the phthalide derivatives according to the invention are utilized may be produced in a similar manner to any of those disclosed in Japanese Patent Publications Nos. 24,188 of 1963, 10,550 of 1970, 13,258 of 1970, 204 of 1974, 6,212 of 1974 and 28,449 of 1974 and Japanese Laid-Open Patent Publications Nos. 31,615 of 1972, 32,532 of 1973, 9,227 of 1974, 135,617 of 1974, 80,120 of 1975, 87,317 of 1975 and 126,228 of 1975.

The invention is also applicable to other recording systems, such as, the ultrasonic record material, e.g., as disclosed in French Patent Specification No. 2,120,992, the electron beam recording system, e.g., as disclosed in Belgian Patent No. 7,959,986, the electrostatic record material, e.g., as disclosed in Japanese Patent Publication No. 3,932 of 1974, the photosensitive printing material, e.g., as disclosed in Japanese Laid-Open Patent Publication No. 12,104 of 1973, the seal stamping material, e.g., as disclosed in Japanese Patent Publication No. 10,766 of 1972, typewriter ribbons as disclosed in Japanese Laid-Open Patent Publication No. 3,713 of 1974, ball-point pen ink as disclosed in Japanese Laid-Open Patent Publication No. 83,924 of 1973 and crayon as disclosed in U.S. Patent Specification No. 3,769,045, by merely using the phthlide derivatives instead of the conventional basic colorless chromogenic materials.

PREFERRED EMBODIMENTS OF THE INVENTION

The following examples serve to illustrate the invention in more detail although the invention is not limited to the examples. Unless otherwise indicated, parts and % signify parts by weight and % by weight, respectively.

EXAMPLE 1

6.3 g of 3,4,5,6-tetrachlorophthalic anhydride and 14.8 g of 1,1-bis(julolidine-9-yl)ethylene were added to 25 g of acetic anhydride and the mixture was heated at 80° C. for one hour. After the termination of reaction, the product was poured into water and then neutralized with an aqueous solution of ammonium to decompose acetic anhydride. The resultant precipitate was separated by filtration. The solid was dried and then recrystallized from o-dichlorobenzene to obtain 13.8 g of 3,3-bis[1,1-bis(julolidine-9-yl)ethylene-2-yl]-4,5,6,7-tetrachlorophthalide in the form of pale yellow crystals having a decomposition temperature of 192°~201° C. The phthalide derivative became green contact with silica gel.

EXAMPLE 2

Example 1 was repeated except that 10.2 g of 3,4,5,6-tetrabromophilic anhydride was used instead of 6.3 g of 3,4,5,6-tetrachlorophthalic anhydride to obtain 15.9 g of 3,3-bis[1,1-bis(julolidine-9-yl)ethylene-2-yl]-4,5,6,7-tetrabromophthalide in the form of yellow crystals having a decomposition temperature of 212°~220° C. The phthalide derivative became green contact with silica gel.

EXAMPLE 3

Example 1 was repeated except that 8.3 g of 4,5-dichloro-3,6-dibromophthalic anhydride was used instead of 6.3 g of 3,4,5,6-tetrachlorophthalic anhydride to obtain 14.2 g of 3,3-bis[1,1-bis(julolidine-9-yl)ethylene-2-yl]-5,6-dichloro-4,7-dibromophthalide in the form of pale yellow crystals having a decomposition temperature of 202°~211° C. The phthalide derivative became green contact with silica gel.

EXAMPLE 4

Example 1 was repeated except that 12.7 g of 1,1-bis-(1-methyl-1,2,3,4-tetrahydroquinoline-6-yl)ethylene was used instead of 14.8 g of 1,1-bis(julolidine-9-yl)ethylene to obtain 16.0 g of 3,3-bis[1,1-bis(1-methyl-1,2,3,4-tetrahydroquinoline-6-yl)ethylene-2-yl]-4,5,6,7-tetrachlorophthalide in the form of pale yellow crystals having a decomposition temperature of 183°~190° C. The phthalide derivative became green contact with silica gel.

EXAMPLE 5

8.3 g of 4,5-dichloro-3,6-dibromophthalic anhydride and 12.8 g of 1,1-bis(4-pyrrolidinophenyl)ethylene were added to 30 g of acetic anhydride and the mixture was heated at 80° C. for one hour. After the termination of reaction, the product was poured into water and then neutralized with an aqueous solution of ammonium to decompose acetic anhydride. The resultant precipitate was separated by filtration. The solid was dried and then recrystallized from o-dichlorobenzene to obtain 15.9 g of 3,3-bis[1,1-bis-(4-pyrrolidinophenyl)ethylene-2-yl]-5,6-dichloro-4,7-dibromophthalide in the form of pale yellow crystals having a decomposition temperature of 195°~200° C. The phthalide derivative became green contact with silica gel.

EXAMPLE 6

Example 5 was repeated except that 8.3 g of 3,6-dichloro-4,5-dibromophthalic anhydride was used instead of 8.3 g of 4,5-dichloro-3,6-dibromophthalic anhydride to obtain 14.8 g of 3,3-bis[1,1-bis(4-pyrrolidinophenyl)-ethylene-2-yl]-4,7-dichloro-5,6-dibromophthalide in the form of pale yellow crystals having a decomposition temperature of 214°~220° C. The phthalide derivative became green contact with silica gel.

EXAMPLE 7

Example 5 was repeated except that 9.2 g of 4-chloro-3,5,6-tribromophthalic anhydride was used instead of 8.3 g of 4,5-dichloro-3,6-dibromophthalic anhydride to obtain 17.2 g of a mixture of 3,3-bis[1,1-bis(4-pyrrolidinophenyl)ethylene-2-yl]-5-chloro-4,6,7-tribromophthalide and 3,3-bis[1,1-bis(4-pyrrolidinophenyl)ethylene-2-yl]-6-chloro-4,5,7-tribromophthalide in the form of pale yellow crystals having a decomposition temperature of 183°~190° C. The phthalide derivative became green contact with silica gel.

EXAMPLE 8

A heat-sensitive record material was prepared by the following method with the use of 3,3-bis[1,1-bis-(julolidine-9-yl)ethylene-2-yl]-4,5,6,7-tetrachlorophthalide obtained in Example 1.

(1) Preparation of A Liquid

The following composition was passed through a sand mill.

| | |
|---|---|
| phthalide derivative obtained in Example 1 | 10 parts |
| 5% aqueous solution of methylcellulose | 5 parts |
| water | 40 parts |

Pulverization was continued until an average particle size of 3 microns.

(2) Preparation of B Liquid

The following composition was passed through a sand mill.

| | |
|---|---|
| 4,4'-isopropylidenediphenol | 20 parts |
| 5% aqueous solution of methylcellulose | 5 parts |
| water | 55 parts |

Pulverization was continued until an average particle size of 3 microns.

(3) Preparation of C Liquid

The following composition was passed through a sand mill.

| | |
|---|---|
| stearic acid amide | 20 parts |
| 5% aqueous solution of methylcellulose | 5 parts |
| water | 55 parts |

Pulverization was continued until an average particle size of 3 microns.

(4) Making a heat-sensitive record material

The following composition was mixed to prepare a coating composition.

| | |
|---|---|
| A liquid | 55 parts |

| | | |
|---|---|---|
| B liquid | 80 parts | |
| C liquid | 80 parts | |
| silicone dioxide pigment (oil absorption: 180 ml/100 g) | 15 parts | |
| 20% aqueous solution of oxidized starch | 50 parts | |
| water | 10 parts | |

The coating composition was coated on a base sheet of 50 g/m² in the weight of an amount of 6 g/m² on dry basis to obtain a heat-sensitive record material.

EXAMPLE 9

Example 8 was repeated except that 3,3-bis[1,1-bis-(julolidine-9-yl)ethylene-2-yl]-4,5,6,7-tetrabromophthalide obtained in Example 2 was used instead of 3,3-bis[1,1-bis-(julolidine-9-yl)ethylene-2-yl]-4,5,6,7-tetrachlorophthalide to obtain a heat-sensitive record material.

EXAMPLE 10

Example 8 was repeated except that 3,3-bis[1,1-bis-(julolidine-9-yl)ethylene-2-yl]-5,6-dichloro-4,7-dibromophthalide obtained in Example 3 was used instead of 3,3-bis[1,1-bis-(julolidine-9-yl)ethylene-2-yl]-4,5,6,7-tetrachlorophthalide to obtain a heat-sensitive record material.

EXAMPLE 11

Example 8 was repeated except that 3,3-bis[1,1-bis-(1-methyl-1,2,3,4-tetrahydroquinoline-6-yl)ethylene-2-yl]-4,5,6,7-tetrachlorophthalide obtained in Example 4 was used instead of 3,3-bis[1,1-bis(julolidine-9-yl)ethylene-2-yl]-4,5,6,7-tetrachlorophthalide to obtain a heat-sensitive record material.

EXAMPLE 12

Example 8 was repeated except that 3,3-bis[1,1-bis-(4-pyrrolidinophenyl)ethylene-2-yl]-5,6-dichloro-4,7-dibromophthalide obtained in Example 5 was used instead of 3,3-bis-[1,1-bis(julolidine-9-yl)ethylene-2-yl]-4,5,6,7-tetrachlorophthalide to obtain a heat-sensitive record material.

EXAMPLE 13

Example 8 was repeated except that 3,3-bis(1,1-bis-(4-pyrrolidinophenyl)ethylene-2-yl]-4,7-dichloro-5,6-dibromophthalide obtained in Example 6 was used instead of 3,3-bis-[1,1-bis(julolidine-9-yl)ethylene-2-yl]-4,5,6,7-tetrachlorophthalide to obtain a heat-sensitive record material.

EXAMPLE 14

Example 8 was repeated except that the mixture of 3,3-bis-[1,1-bis(4-pyrrolidinophenyl)ethylene-2-yl]-5-chloro-4,5,7-tribromophthalide and 3,3-bis[1,1-bis(4-pyrrolidinophenyl)-ethylene-2-yl]-6-chloro-4,5,7-tribromophthalide obtained in Example 7 was used instead of 3,3-bis[1,1-bis(julolidine-9-yl)-ethylene-2-yl]-4,5,6,7-tetrachlorophthalide to obtain a heat-sensitive record material.

CONTROL 1

Example 8 was repeated except that 3,3-bis[1,1-bis-(4-pyrrolidinophenyl)ethylene-2-yl]-4,5,6,7-tetrachlorophthalide was used instead of 3,3-bis[1,1-bis(julolidine-9-yl)-ethylene-2-yl]-4,5,6,7-tetrachlorophthalide to obtain a heat-sensitive record material.

CONTROL 2

Example 8 was repeated except that 3,3-bis[1,1-bis-(4-pyrrolidinophenyl)ethylene-2-yl]-4,5,6,7-tetrabromophthalide was used instead of 3,3-bis[1,1-bis(julolidine-9-yl)-ethylene-2-yl]-4,5,6,7-tetrachlorophthalide to obtain a heat-sensitive record material.

The following properties of thus obtained nine heat-sensitive record materials were examined. The results are shown in Table 1.

(1) Fogging at Near Infrared Region

The optical density of the coated surface of each record materials before recording was measured at 830 nm with a spectrophotometer.

(2) Color Developability at Near Infrared Region

Each record material was stayed on heated plate at 120° C. for 5 seconds with a pressure of 4 kg/cm² to develop a green color image. The optical density (initial density) of the color image was measured in the same manner as in the above test 1.

(3) Moisture Resistance at Near Infrared Region

After the record materials before recording were allowed to stand at 50° C. under 90% RH for 24 hours, the optical density of the coated surface of each record materials before recording was measured in the same manner as in the above test 1.

(4) Heat Resistance at Near Infrared Region

The record materials after the above color developing test 2 were allowed to stand at 60° C. for 24 hours, and then the optical density of the non-recorded coating layer (smudges by heating) and the optical density of the developed color images were measured in the same manner as in the above test 1. The discoloration degree was calculated by the following equation.

$$\frac{\text{(initial density)} - \text{(density after heating)}}{\text{(initial density)}} \times 100(\%)$$

(5) Light Resistance at Near Infrared Region

The color images obtained in the above color developing test 2 were exposed to sun light for 5 hours and then the optical density of them was measured in the same manner as in the above test 1. Further, the discoloration degree was calculated by the following equation.

$$\frac{\text{(initial density)} - \text{(density after exposing to sun light)}}{\text{(initial density)}} \times 100(\%)$$

TABLE 1

| | | Color*2 | | | Heat Resistance | | | Light Resistance | |
|---|---|---|---|---|---|---|---|---|---|
| | Fogging*1 | Develop-ability | Moisture*3 Resistance | I*4 | II*5 | Discoloration Degree | III*6 | Discoloration Degree | |
| Example 8 | 0.04 | 0.93 | 0.09 | 0.16 | 0.75 | 19.4 | 0.81 | 12.9 | |

TABLE 1-continued

|  | Color*2 | | Moisture*3 Resistance | Heat Resistance | | | Light Resistance | |
|---|---|---|---|---|---|---|---|---|
|  | Fogging*1 | Develop-ability |  | I*4 | II*5 | Discoloration Degree | III*6 | Discoloration Degree |
| Example 9 | 0.05 | 0.92 | 0.12 | 0.14 | 0.72 | 21.7 | 0.83 | 9.8 |
| Example 10 | 0.07 | 0.92 | 0.10 | 0.11 | 0.83 | 9.8 | 0.79 | 14.1 |
| Example 11 | 0.04 | 0.93 | 0.10 | 0.15 | 0.73 | 21.5 | 0.82 | 11.8 |
| Example 12 | 0.05 | 0.93 | 0.12 | 0.09 | 0.90 | 3.2 | 0.76 | 18.3 |
| Example 13 | 0.05 | 0.92 | 0.13 | 0.09 | 0.89 | 3.3 | 0.74 | 19.6 |
| Example 14 | 0.04 | 0.93 | 0.09 | 0.08 | 0.92 | 1.1 | 0.80 | 14.0 |
| Control 1 | 0.07 | 0.92 | 0.32 | 0.17 | 0.68 | 26.1 | 0.41 | 55.4 |
| Control 2 | 0.06 | 0.92 | 0.15 | 0.15 | 0.53 | 42.4 | 0.65 | 29.3 |

*1Optical density of record materials before recording.
*2Optical density of recorded images (initial density).
*3Optical density of record materials before recording and after treatment under 90% RH.
*4Optical density of the non-recorded portion after treatment at 60° C.
*5Optical density of the color images after treatment at 60° C.
*6Optical density of the color images after exposing to sun light.

EXAMPLE 15

A pressure-sensitive record material was prepared by the following method with the use of 3,3-bis[1,1-bis-(julolidine-9-yl)ethylene-2-yl]-4,5,6,7-tetrachlorophthalide obtained in Example 1.

3 parts of the above phthalide derivative was dissolved in 100 parts of isopropylated naphthalene. The resultant solution was dispersed in 350 parts of warm water (50° C.) containing 25 parts of pigskin-gelatin having an isoelectric point of 8 and 25 parts of gum arabic dissolved in it to obtain an emulsion. 1000 parts of warm water was added to the emulsion. The mixture was adjusted to pH 4 with acetic acid and cooled at 10° C. 10 parts of 25% aqueous solution of glutaraldehyde was added to it to solidify capsules. The capsule-containing coating composition was coated on one surface of a base sheet of 45 g/m² in the weight of 5 g/m² on dry basis and an acceptor coating composition comprising 20 parts of zinc 3,5-bis(α-methylbenzyl)salicylate, 80 parts of kaolin and 30 parts of styrene-butadiene copolymer emulsion (solid content: 50%) dispersed in 200 parts of water was coated on another surface of the base sheet in the weight of 5 g/m² on dry basis to obtain a pressure-sensitive record material (middle sheet).

Several of the pressure-sensitive record material were piled in the manner as the capsule coated layer was closed to the acceptor coated layer, pressed with driving a pen to obtain green images on the acceptor coated surface. The color images were stable to water and alcohol and, when exposed to sunlight, the color change and discolouration were not appreciated. The light absorption spectrum had a broad strong absorption at 590~850 nm.

EXAMPLE 16

A pressure-sensitive record material was prepared in the same manner as in Example 15 except that the mixture of 3,3-bis[1,1-bis(4-pyrrolidinophenyl)ethylene-2-yl]-5-chloro-4,6,7-tribromophthalide and 3,3-bis[1,1-bis(4-pyrrolidinophenyl)ethylene-2-yl]-6-chloro-4,5,7-tribromophthalide obtained in Example 7 was used instead of 3,3-bis[1,1-bis(julolidine-9-yl)ethylene-2-yl]-4,5,6,7-tetrachlorophthalide.

Several of the pressure-sensitive record material were piled in the manner as the capsule coated layer was closed to the acceptor coated layer, pressed with driving a pen to obtain green images on the acceptor coated surface. The color images were stable to water and alcohol and, when exposed to sunlight, the color change and discolouration were not appreciated. The light absorption spectrum had a broad strong absorption at 590~850 nm.

EXAMPLE 17

An electrothermal record material was prepared by the following method with the use of the phthalide derivative obtained in Example 4.

200 parts of cuprous iodide and 5 parts of 10% aqueous solution of sodium sulfite were added to 200 parts of 1% aqueous solution of polyvinyl alcohol. The mixture was passed through a sand mill. Pulverization was continued until an average particle size of 2 microns. To the pulverized mixture 8 parts of polyacrylate emulsion and 20 parts of titanium dioxide were added and thoroughly dispersed. The dispersion was coated on a base sheet of 50 g/m² in the weight of 7 g/m² on dry basis. Further, there was coated on the coating layer in the weight of 5 g/m² on dry basis a heat-sensitive coating composition prepared in Example 11 with the use of 3,3-bis[1,1-bis(1-methyl-1,2,3,4-tetrahydroquinoline-6-yl)ethylene-2-yl]-4,5,6,7-tetrachlorophthalide obtained in Example 4 to obtain an electrothermal record material.

Images were recorded on the record material with the use of a cylindrical scanning recording machine at a scanning speed of 630 mm/sec with a needle pressure of 10 g. The recorded images were deep green and superior in light resistance. The light absorption spectrum of them had a broad strong absorption at 620~850 nm.

EXAMPLE 18

An electrothermal record material was prepared in the same manner as in Example 17 except that the phthalide derivative obtained in Example 5 was used instead of 3,3-bis[1,1-bis(1-methyl-1,2,3,4-tetrahydroquinoline-6-yl)-ethylene-2-yl]-4,5,6,7-tetrachlorophthalide.

Images were recorded on the record material with the use of a cylindrical scanning recording machine at a scanning speed of 630 mm/sec with a needle pressure of 10 g. The recorded images were deep green and superior in light resistance. The light absorption spectrum of them had a strong absorption at 475 nm and a broad strong absorption at 625~850 nm.

EXAMPLE 19

A phtosensitive record material was prepared by the following method with the use of the phthalide derivative obtained in Example 3.

6 g of 3,3-bis[1,1-bis(julolidine-9-yl)ethylene-2-yl]-5,6-dichloro-4,7-dibromophthalide obtained in Example 3 was dissolved in 40 ml of chloroform. 40 ml of 10% benzene solution of polystyrene and 5 g of carbon tetrabromide were added to the solution and the mixture was thoroughly stirred to prepare a coating composition, the coating composition was coated on polyethylene laminated paper having polyethylene at the both surfaces in the weight of 5 g/m² on dry basis in a dark place. The coated paper was irradiated with a light of eight ultraviolet lamps of 20 W from a distance of 5 cm for 10 minutes to develop green color images. The color images were then fixed by rinsing with a solution of acetone/n-hexane (1/5). The resultant images were stable when exposed to sunlight and the light absorption spectrum had a broad strong absorption at 625~850 nm.

EXAMPLE 20

A photosensitive record material was prepared in the same manner as in Example 19 except that 3,3-bis[1,1-bis(4-pyrrolidinophenyl)ethylene-2-yl]-4,7-dichloro-5,6-dibromophthalide obtained in Example 6 was used instead of 3,3-bis[1,1-bis(julolidine-9-yl)ethylene-2-yl]-5,6-dichloro-4,7-dibromophthalide.

The green images developed on the record material in the same manner as in Example 19 were stable when exposed to sunlight and the light absorption spectrum had a strong absorption at 475 nm and a broad strong absorption at 625~850 nm.

EXAMPLE 21

An ultrasonic vibrator of needle type having a radius of 0.2 mm was slightly contacted on a surface of the heat-sensitive record material obtained in Example 8 and the record material was moved at a speed of 20 cm/sec under an ultrasonic vibration of 19 KHz 20 W to obtain green recorded images superior in light resistance.

EXAMPLE 22

An ultrasonic vibrator of needle type having a radius of 0.2 mm was slightly contacted on a surface of the heat-sensitive record material obtained in Example 12 and the record material was moved at a speed of 20 cm/sec under an ultrasonic vibration of 19 KHz 20 W to obtain green recorded images superior in light resistance.

What we claim is:

1. A phthalide derivative having the following formula:

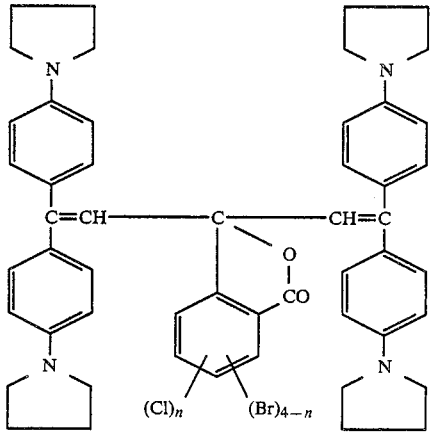

wherein n is an integer of 1 to 3.

* * * * *